United States Patent
Tang et al.

(10) Patent No.: US 7,173,996 B2
(45) Date of Patent: Feb. 6, 2007

(54) METHODS AND APPARATUS FOR 3D RECONSTRUCTION IN HELICAL CONE BEAM VOLUMETRIC CT

(75) Inventors: Xiangyang Tang, Waukesha, WI (US); Jiang Hsieh, Brookfield, WI (US); Roy Arnulf Helge Nilsen, Menomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 228 days.

(21) Appl. No.: 10/892,931

(22) Filed: Jul. 16, 2004

(65) Prior Publication Data
US 2006/0013357 A1    Jan. 19, 2006

(51) Int. Cl.
*G01N 23/00* (2006.01)
(52) U.S. Cl. .......................................... 378/15; 378/901
(58) Field of Classification Search ................... 378/15, 378/4–20, 901
See application file for complete search history.

(56) References Cited

U.S. PATENT DOCUMENTS

| | | | | |
|---|---|---|---|---|
| 5,390,112 | A | 2/1995 | Tam | 378/17 |
| 6,263,040 | B1 | 7/2001 | Hsieh | 378/15 |
| 6,266,388 | B1 | 7/2001 | Hsieh | 378/8 |
| 6,269,139 | B1 | 7/2001 | Hsieh | 378/4 |
| 6,408,042 | B1 | 6/2002 | Hsieh | 378/4 |
| 6,421,411 | B1 | 7/2002 | Hsieh | 378/4 |
| 6,452,996 | B1 | 9/2002 | Hsieh | 378/15 |
| 6,490,333 | B1 | 12/2002 | Hsieh | 378/4 |
| 6,504,892 | B1 * | 1/2003 | Ning | 378/4 |
| 6,507,632 | B1 | 1/2003 | Hsieh | 378/4 |
| 6,560,308 | B1 | 5/2003 | Zmora | 378/4 |
| 6,584,165 | B1 | 6/2003 | Wang et al. | 378/4 |
| 6,597,756 | B1 | 7/2003 | Basu et al. | 378/15 |
| 6,600,802 | B1 | 7/2003 | Hsieh | 378/4 |
| 6,654,440 | B1 | 11/2003 | Hsieh | 378/4 |
| 6,654,442 | B2 | 11/2003 | Hsieh | 378/15 |
| 6,678,346 | B2 | 1/2004 | Hsieh | 378/4 |
| 6,754,300 | B2 | 6/2004 | Hsieh et al. | 378/16 |
| 6,778,630 | B2 * | 8/2004 | Silver et al. | 378/15 |
| 6,845,144 | B2 * | 1/2005 | Nishide et al. | 378/15 |
| 6,917,663 | B2 * | 7/2005 | Taguchi et al. | 378/15 |
| 2003/0068015 | A1 * | 4/2003 | Bruder et al. | 378/210 |
| 2003/0073893 | A1 | 4/2003 | Hsieh | 600/407 |

(Continued)

OTHER PUBLICATIONS

Performance of approximate cone-beam reconstruction in mulit-slice computed tomography, Bruder et al., 2000, In Medical Imaging, vol. 3979.*

(Continued)

*Primary Examiner*—Courtney Thomas
*Assistant Examiner*—Alexander Taningco
(74) *Attorney, Agent, or Firm*—Carl B. Horton; Armstrong Teasdale, LLP (57) ABSTRACT

A method for reconstructing an image of an object utilizing a cone-beam volumetric computed tomographic imaging apparatus includes helically scanning the object with a radiation source utilizing the cone-beam volumetric computed tomographic imaging apparatus; selecting radiation beams emitted by the radiation source passing through a pixel P having a smallest cone angle in comparison with that of the conjugate rays of the radiation beam; and reconstructing an image of the object utilizing projection data obtained from the selected radiation beams while avoiding the use of redundant projection data from unselected conjugate rays of the selected radiation beams.

24 Claims, 6 Drawing Sheets

U.S. PATENT DOCUMENTS

| | | | |
|---|---|---|---|
| 2003/0185337 A1 | 10/2003 | Hsieh | 378/4 |
| 2003/0223533 A1 | 12/2003 | Hsieh et al. | 375/19 |
| 2003/0235267 A1 | 12/2003 | Hsieh et al. | 378/16 |
| 2004/0066911 A1 | 4/2004 | Hsieh et al. | 378/210 |
| 2004/0073584 A1 | 4/2004 | Hsieh et al. | 708/200 |
| 2006/0104407 A1* | 5/2006 | Zamyatin et al. | 378/4 |

OTHER PUBLICATIONS

Advanced single-slice rebinning in cone-beam spiral CT, Kachelrieß et al., Apr. 2000, Med. Phys., 27(4).*

Katsevich, Alexander; "Analysis of an Exact Inversion Algorithm for Spiral Cone-Beam CT"; *Physics in Medicine and Biology*; pp. 2583-2597; 47; 2002.

Danielsson, Per-Erik; Magnusson Seger, Maria; and Turbell, Henrick; "The PI-Methods for Helical Cone-Beam Tomography"; *Physics in Medicine and Biology.*; pp. 1(14)-14(14); Submitted Dec. 2001.

Danielsson, Per-Erik; Edholm, Paul; Eriksson, Jan; Magnusson Seger, Maria; "Towards Exact 3D-reconstruction for Helical Cone-Beam Scanning of Long Objects. A New Detector Arrangement and a New Completeness Condition"; "*International Meeting on Fully Three-Dimensional Image Reconstruction in Radiology and Nuclear Medicine*"; Pittsburgh, PA; Jun. 25-28, 1997, pp 141-144.

\* cited by examiner

PRIOR ART

METHODS AND APPARATUS FOR 3D RECONSTRUCTION IN HELICAL CONE BEAM VOLUMETRIC CT

BACKGROUND OF THE INVENTION

This invention relates generally to methods and apparatus for reconstruction of volumetric computed tomographic (CT) images, and more particularly to methods and apparatus for helical cone beam volumetric CT image reconstruction with three dimensional (3D) reconstruction view windowing to reduce or eliminate data redundancy.

In at least one known multi-detector row CT imaging systems, two-dimensional (2D) algorithms have been used to reconstruct tomographic images based on an approximation of cone beam (CB) geometry into fan beam (FB) geometry. As CB volumetric CT (VCT) technology becomes more prevalent, maintaining reconstruction accuracy has become more challenging. As a result of a significantly larger cone angle, CB-to-FB geometry approximations result in significant artifacts. To combat these artifacts, three dimensional (3D) reconstruction algorithms can be used in CB VCT. One such algorithm has been proposed by A. Katsevich in "Analysis of an exact inversion algorithm for spiral cone-beam CT," Physics in Medicine & Biology vol. 47, pp. 2583–2598, 2002. A common feature of these helical CB reconstruction algorithms is the utilization of the view windowing function known as the "Tam window" to handle data redundancy. See, for example, U.S. Pat. No. 5,390,112 (assigned to General Electric) entitled "Three-dimensional computerized tomography scanning method and system for imaging large objects with smaller area detectors," and P. E. Danielsson, P.-E., P. Edholm, J. Eriksson, and M. Magnusson-Seger, "Towards exact 3D-reconstruction for helical cone-beam scanning of long objects: A new arrangement and a new completeness condition," International Meeting on Fully Three-dimensional Image Reconstruction in Radiology and Nuclear Medicine, Jun. 25–28, 1997.

More specifically, in a helical CB reconstruction, given a segment of a source trajectory, the data redundancy of a pixel in a field of view (FOV) that is in a plane orthogonal to the axis of the helical source trajectory, is location-dependent. Such a location-dependent data redundancy is non-uniform within an FOV, resulting in substantial shading and/or glaring artifacts in reconstructed images. Hence, handling data redundancy appropriately is one of the more challenging aspects of helical CB reconstruction. The most straightforward approach is to remove all data redundancy, such as by using Tam-windows.

Fundamentally, the Tam-window discards all redundant data by windowing a helical projection, because the projection data corresponding to an x-ray is exclusively within or outside the Tam-window. Theoretically, the analytic Tam-window is accurate in handling data redundancy in helical CB reconstruction. However, the implementation of the analytic Tam-window in the detector of a CB VCT scanner is actually a discrete sampling of the analytic one because of the finite dimension of detector elements. Thus, special care is needed to appropriately carry out such a discrete sampling. In fact, it has been found that a direct utilization of the Tam-window results in unexpected, substantial artifacts in tomographic images that have to be suppressed by extra compensation measures.

BRIEF DESCRIPTION OF THE INVENTION

There is therefore provided, in some configurations of the present invention, a method for reconstructing an image of an object utilizing a cone-beam volumetric computed tomographic imaging apparatus. The method includes helically scanning the object with a radiation source utilizing the cone-beam volumetric computed tomographic imaging apparatus, selecting radiation beams emitted by the radiation source passing through a pixel P having a smallest cone angle in comparison with that of the conjugate rays of the radiation beam, and reconstructing an image of the object utilizing projection data obtained from the selected radiation beams.

In another aspect, some configurations of the present invention provide a cone-beam volumetric computed tomographic imaging apparatus. The apparatus is configured to helically scan an object to be imaged with a radiation source, select radiation beams emitted by the radiation source passing through a pixel P having a smallest cone angle in comparison with that of the conjugate rays of the radiation beam, and reconstruct an image of the object utilizing projection data obtained from the selected radiation beams.

Configurations of the present invention will be seen to provide alternatives to the well-known Tam-window for CB volumetric CT utilizing exact and approximate helical CB reconstruction methods to handle data redundancy. Moreover, by avoiding a discrete sampling of the Tam-window, artifacts introduced in tomographic images are substantially reduced.

DETAILED DESCRIPTION OF THE INVENTION

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
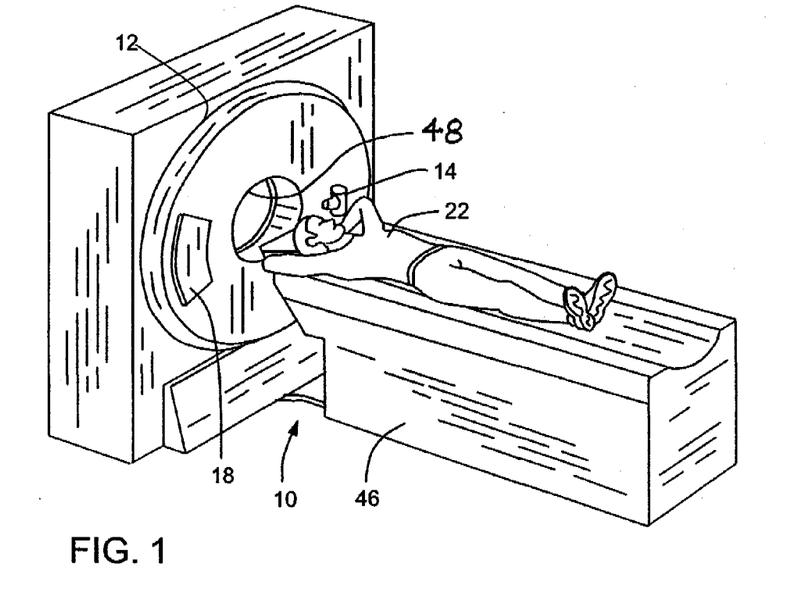
FIG. 1 is a pictorial drawing representative of some configurations of CT imaging apparatus of the present invention.
Figure 2:
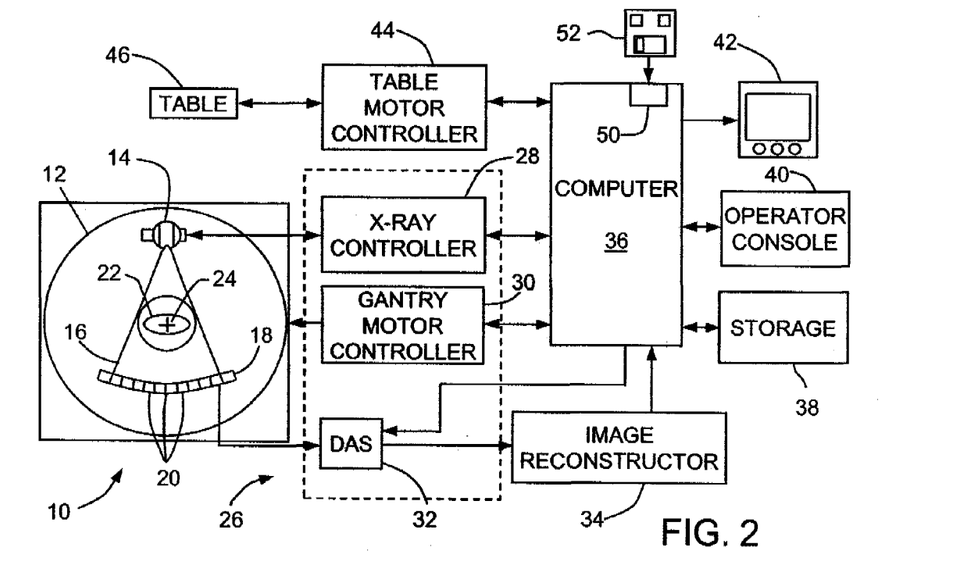
FIG. 2 is a functional block diagram representative of the CT imaging apparatus of FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 or other suitable display type allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector-rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Some configurations of the present invention provide a view windowing alternative to the Tam-window for helical HB reconstruction. Rather than comparing each x-ray passing through a pixel in an image to be reconstructed with the boundary of the Tam-window, some configurations of the present invention pick up the x-ray with the smallest cone angle only. Although the method used to handle helical projection data redundancy is quite different from that of the Tam-window technique, a similar result is achieved, namely the discarding of redundant projection data in the helical 3D backprojection. As a result, technical effects of various configurations of the present invention include, among other things, a reduction or elimination of artifacts in tomographic images reconstructed by other known methods. Configurations of the present invention can be used in applications in which accurate or approximate CB reconstructions are currently performed using Tam-windows.

Figure 3:
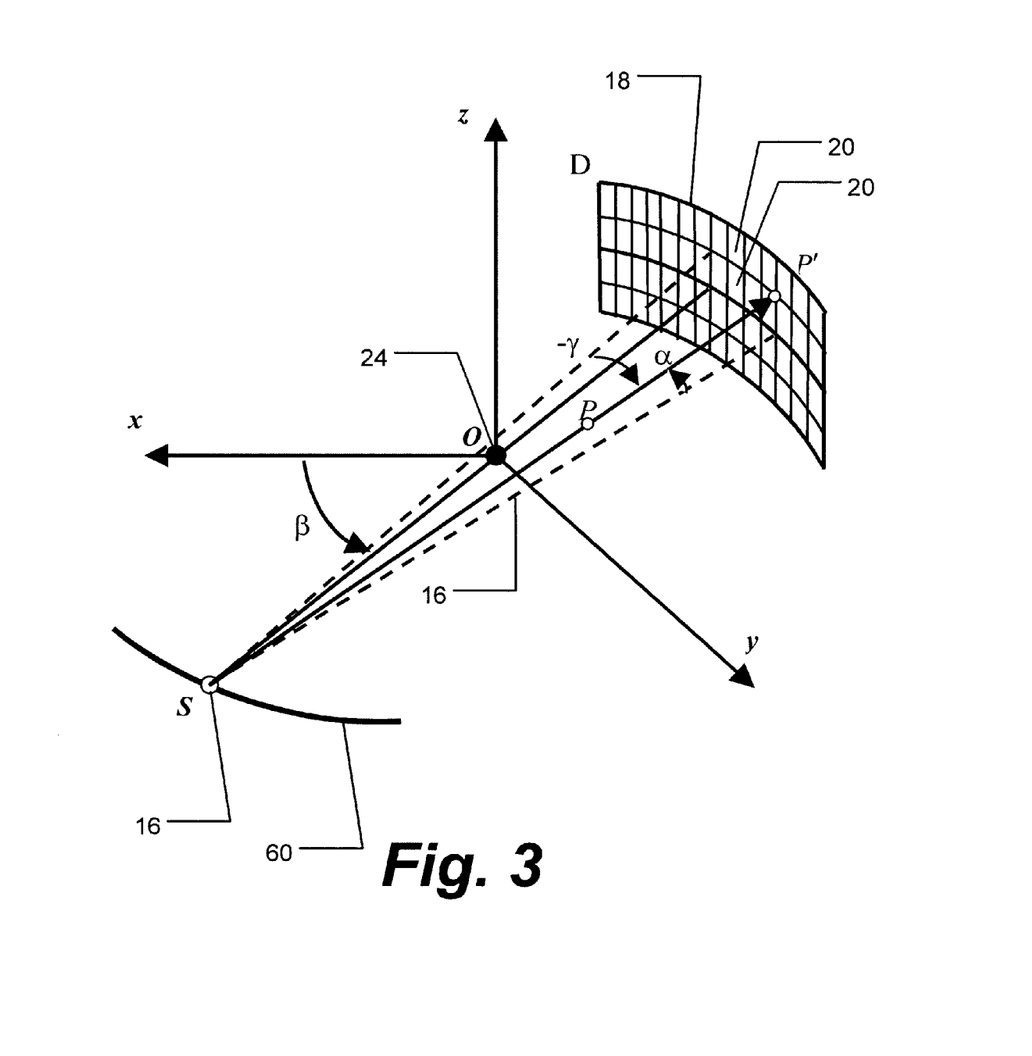
FIG. 3 is a representation of the geometry of a CB VCT apparatus.

In some configurations and referring to the geometry of a CB VCT using a cylindrical radiation detector array 18 as represented in FIG. 3, a radiation beam 16 emanates from a focal spot S of radiation source 14. In many computed tomographic imaging systems 10, radiation detector array 18 is an x-ray detector array, radiation beam 16 is an x-ray beam, and radiation source 14 is an x-ray source, and will be referred to as such herein. However, configurations of the present invention are not limited to the use of x-ray radiation.

Figure 4:
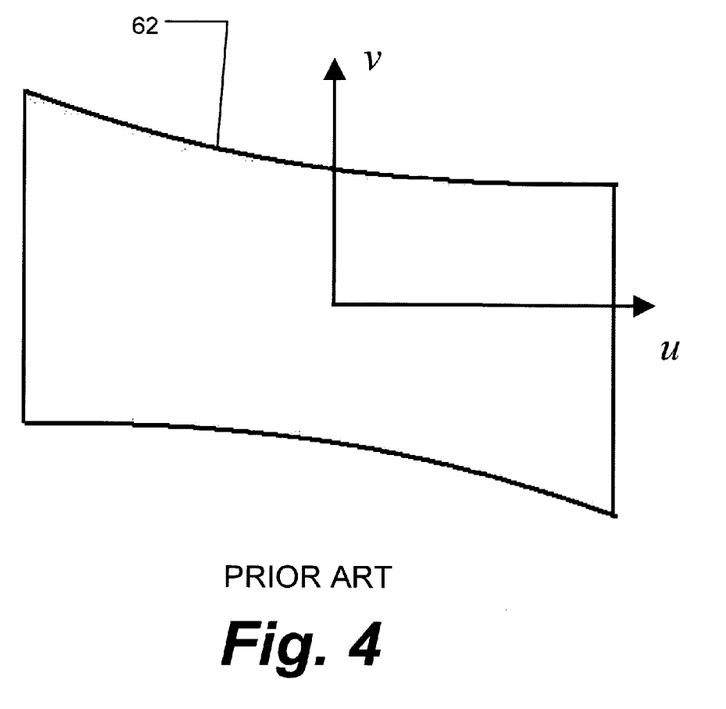
FIG. 4 is an example of a prior art Tam-window.

X-ray beam 16 passes through a point P, and has a view angle $\beta$, a fan angle $\gamma$, and a cone angle $\alpha$. Point P' represents the projection of point P in detector array D (or 18). In the cylindrical detector D (or 18), the well-known Tam-window can be written as:

$$v = \frac{Lh}{R}\left(1 + \frac{u^2}{L^2}\right)\left[\frac{\pi}{2} \pm \arctan\left(\frac{u}{L}\right)\right], \quad (1)$$

where u and v are the horizontal and vertical coordinates, respectively, in cylindrical detector array 18, and L is the distance from source focal spot S of x-ray source 14 to detector D (or 18), R is the distance from source focal spot S to the axis z of helical source trajectory 60, and h is the distance proceeded per helical turn. An example of a prior art Tam-window 62 is shown in FIG. 4. The upper and lower boundaries of Tam-window 62 are determined by the intersection of the x-ray beams emanating from the source and passing through the upper and lower helical turns. It has been mathematically proven that all redundant helical projection data acquired along a helical source trajectory are outside Tam-window 62. As a result, it is guaranteed that no contribution comes from redundant projection data to reconstructed images if one applies Tam-window 62 in projection data acquired along a helical source directory.

In various configurations of the present invention, a virtual/general Tam-window picks up projection data corresponding to the x-ray beam passing through the pixel to be reconstructed at the smallest cone angle.

Figure 5:
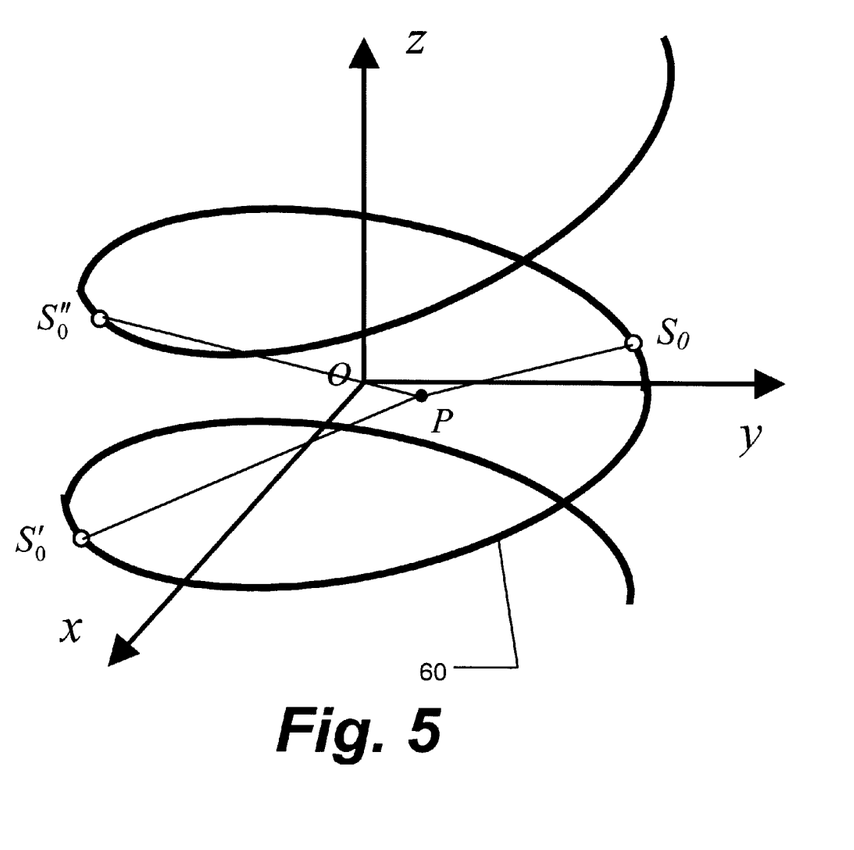
FIG. 5 is a schematic diagram showing the geometry of direct-ray and conjugate-rays of pixel P to be reconstructed by CB reconstruction algorithms based on a helical source trajectory, where ray $S_0P$ is determined by $(\alpha_0, \beta_0, \gamma_0)$, ray $S_0'P$ by $(\alpha_0', \beta_0', \gamma_0')$ and $S_0''P$ by $(\alpha_0'', \beta_0'', \gamma_0'')$, respectively.

A pixel P lies within a reconstruction plane RP that is orthogonal to the axis of the helical source trajectory. Reconstruction plane RP intersects the helical source trajectory at view angle $\beta=0$. Without loss of generality, and referring to FIG. 5, line $S_0P$ (also called a "direct ray"), represents an x-ray beam passing through pixel P at view angle $\beta_0$, ($|\beta_0|\leq\pi$) and cone angle $\alpha_0$. If helical source trajectory 60 extends over one turn, more x-ray beams pass through pixel P at view angle $\beta_i=\beta_0\pm i\cdot 2\pi$ and different cone angle $\alpha_i$, (i=1, 2, 3, . . . ), and these x-ray beams are called co-direct rays corresponding to the direct ray. In addition to the co-direct rays, there exist two other x-ray beams passing through pixel P oppositely in relation to the direct ray with view angle $\beta_0'$ or $\beta_0''$, and cone angle $\alpha_0'$ or $\alpha_0''$, respectively, and these x-ray beams are called conjugate rays corresponding to the direct ray. As an example, two conjugate rays are shown in FIG. 5. Other x-ray beams possessing through pixel P at view angle $\beta_i'=\beta_0'\pm i\cdot 2\pi$ or $\beta_i''=\beta_0''\pm i\cdot 2\pi$ are called co-conjugate rays. More particularly, ray $S_0P$ is determined by $(\alpha_0, \beta_0, \gamma_0)$, ray $S_0'P$ by $(\alpha_0', \beta_0', \gamma_0')$ and $S_0''P$ by $(\alpha_0'', \beta_0'', \gamma_0'')$, respectively.

It is always true that the cone angle of the direct ray is smaller than that of co-direct rays, and the cone angle of the conjugate rays is smaller than that of co-conjugate rays. Therefore, one can pick up the x-ray beam passing through pixel P with the smallest cone angle by comparing its cone angle with that of its conjugate rays. Analytically, in one configuration of the present invention, the virtual/general Tam-window is written:

$$w(\alpha, \beta, \gamma) = \begin{cases} 1 & \text{while } \alpha = \min(\alpha_0, \alpha_0', \alpha_0''), \\ 0 & \text{otherwise.} \end{cases} \quad (2)$$

Without loss of generality, the segment of the helical source trajectory can be restricted within one turn. Letting $\beta_c$, $\alpha_c$ and $\gamma_c$ represent the view angle, cone angle, and fan angle of the conjugate rays, respectively, the relationships $\beta_c=\beta_0'$ and $\alpha_c=\alpha_0'$ hold while $0<\beta_0\leq\pi$, while the relationships $\beta_c=\beta_0''$ and $\alpha_c=\alpha_0''$ hold while $-\pi<\beta_0\leq 0$. As a result, equation (2) can be written:

$$w(\alpha, \beta, \gamma) = \begin{cases} 1 & \text{while } \alpha = \min(\alpha_0, \alpha_c) \\ 0 & \text{otherwise.} \end{cases} \quad (3)$$

Based on the CB geometry represented in FIG. 5, the relationships:

$$\beta_c=\beta_0-\pi+2\cdot\gamma_0 \quad (4)$$

and $$\gamma_c=-\gamma_0 \quad (5)$$

hold while $0<\beta_0\leq\pi$, while the relationships:

$$\beta_c=\beta_0+\pi+2\cdot\gamma_0 \quad (6)$$

and $$\gamma_c=-\gamma_0 \quad (7)$$

hold while $-\pi<\beta_0\leq 0$. In both cases, the cone angles $\alpha_c$ can be easily obtained through geometrical calculations.

Figure 6:
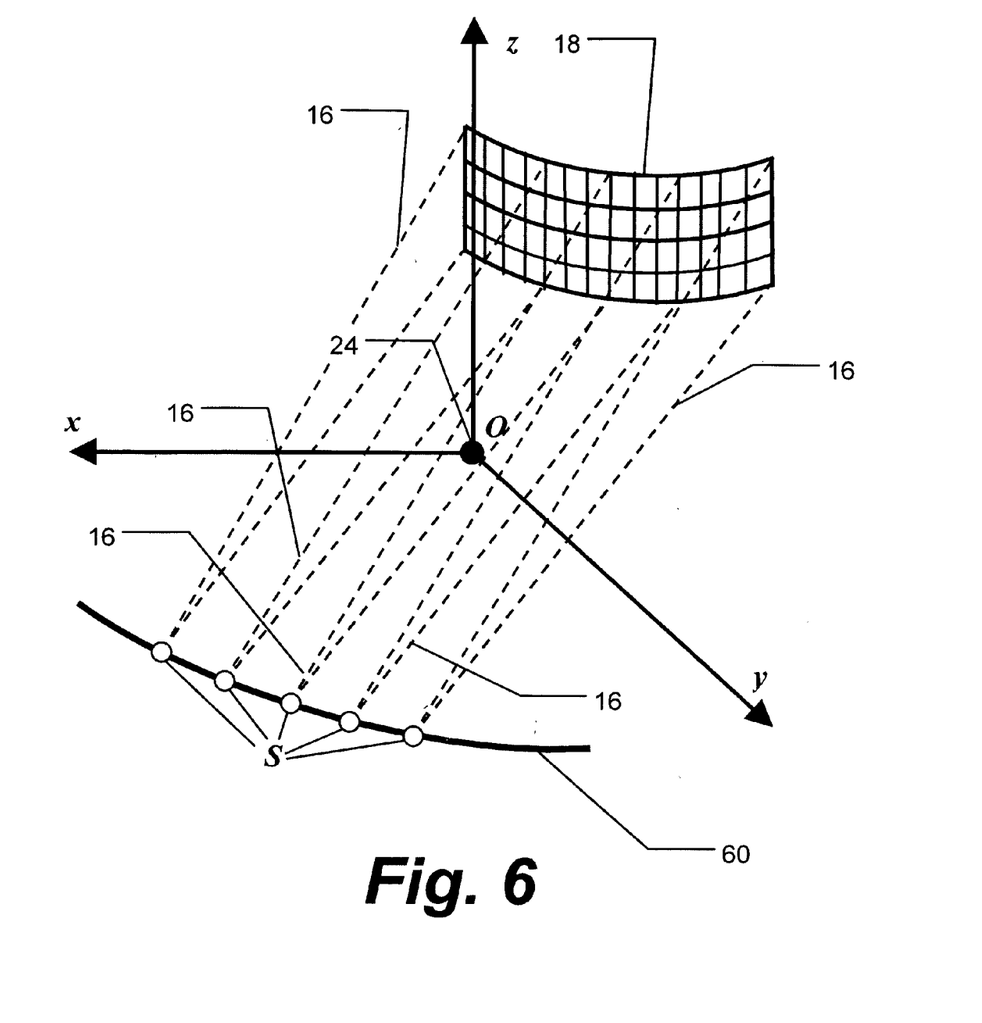
FIG. 6 is a schematic diagram showing the geometry of semi-CB, which can be obtained from the CB projection data acquired by the geometry shown in FIG. 3 through row-wise fan-to-parallel rebinning.

In some configurations, a helical CB reconstruction is provided using a geometry referred to as "semi-CB" shown in FIG. 6, illustrating an x-ray source 14 focal point S at a few positions along a trajectory 60, representing points that focal point S occupies at different times. Several x-ray beams 16 are also illustrated, showing the geometry of the x-ray beams emitted by x-ray source 14 at each different location represented in FIG. 6. The semi-CB geometry is implemented using row-wise fan-to-parallel rebinning of the CB projection data. In configurations using the semi-CB geometry, relationships written:

$$\beta_c = \beta_0 - \pi \quad (8)$$

and $$t_c = -t_0 \quad (9)$$

hold while $0 < \beta_0 \leq \pi$, whereas relationships written:

$$\beta_c = \beta_0 + \pi \quad (10)$$

and $$t_c = -t_0, \quad (11)$$

hold while $-\pi < \beta_0 \leq 0$ wherein $t_0$ represents the orthogonal distance between the direct ray passing through pixel P and axis z, and $t_c$ represents the orthogonal distance between the conjugate ray passing through pixel P and axis z.

The virtual/general Tam-window written in equation (3) is an asymptotic function of:

$$\tilde{w}(\alpha, \beta, \gamma; k) = \frac{|\tan \alpha_c|^k}{|\tan \alpha_0|^k + |\tan \alpha_c|^k}, \text{ i.e.,} \quad (12)$$

$$w(\alpha, \beta, \gamma) = \lim_{k \to +\infty} w(\alpha, \beta, \gamma; k) = \lim_{k \to +\infty} \frac{|\tan \alpha_c|^k}{|\tan \alpha_0|^k + |\tan \alpha_c|^k}. \quad (13)$$

It has been found that $w(\alpha, \beta, \gamma; k)$ can approximate $w(\alpha, \beta, \gamma)$ very well while k is an integer equal to or larger than 64. In other configurations, values of k can be selected (including values less than 64) depending upon whether w( ) is to be used as a windowing function or as a weighting function. More generally, if $f_k(\alpha)$ denotes a positive valued, monotonically increasing function of both $\alpha$ and k, then $f_k(\alpha)$ also has the property that $f_k(\alpha) \to \infty$ when $k \to \infty$. Thus, a weighting function $\tilde{w}( )$ used in some configurations of the present invention is written:

$$\tilde{w}(\alpha, \beta, \gamma) = \frac{f_k(\alpha_c)}{f_k(\alpha_0) + f_k(\alpha_c)}. \quad (14)$$

Figure 7:
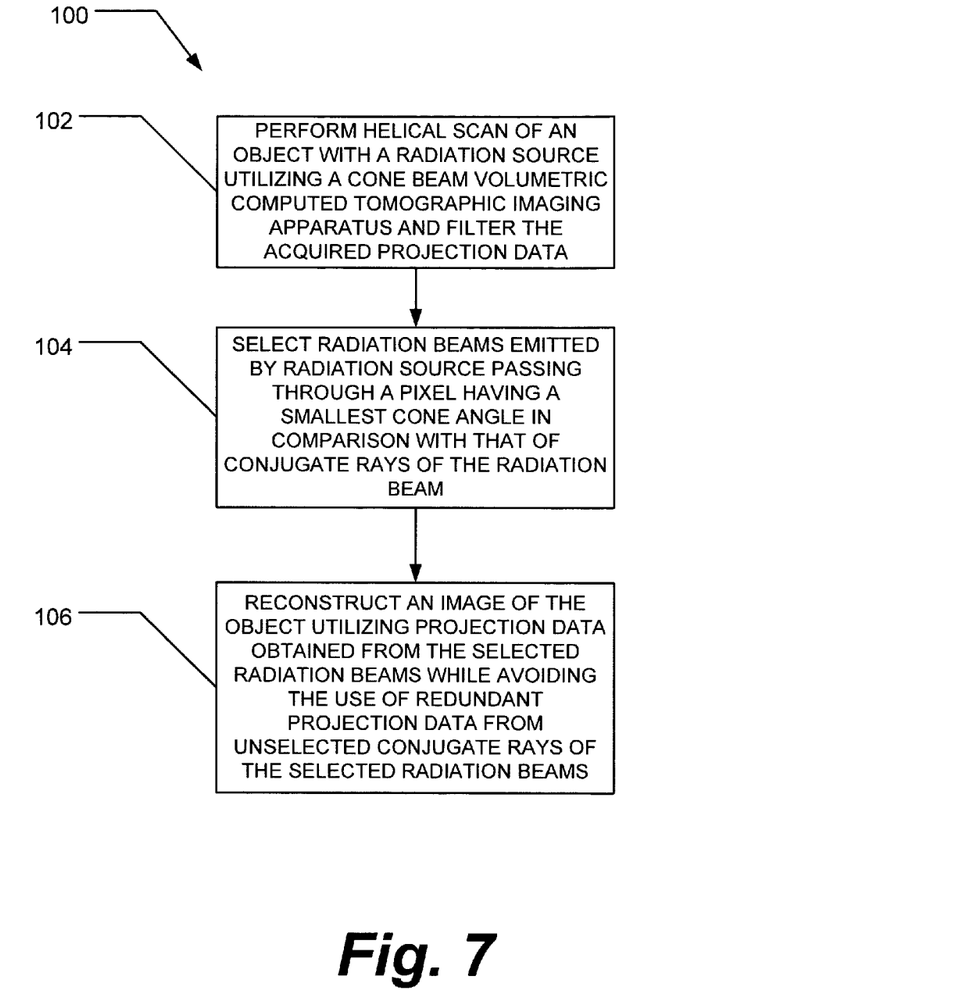
FIG. 7 is a flow chart representative of a method for reconstructing an image of an object in configurations of the present invention.

Thus, and referring to flow chart 100 of FIG. 7, a technical result of the present invention is achieved in some configurations by a user initiating a helical scan of an object 22 (for example, a medical patient) with a radiation source such as radiation source 14 utilizing a cone beam volumetric computed tomographic imaging apparatus 10 at 102 and filtering the acquired projection data. Radiation beams 16 emitted by radiation source 14 are then selected at 104 passing through a pixel P having a smallest cone angle in comparison with that of conjugate rays of the radiation beam. (By "selecting radiation beams," it is meant that a determination is made as to the projection data that is to be used for reconstructing the image of the object, for example, by applying a window function to projection data.) In some configurations, selecting radiation beams passing through pixel P includes windowing the filtered projection data using a configuration of virtual/general Tam-window such as those disclosed herein to avoid conjugate projection data contributing to reconstruction. At 106, an image of the object is reconstructed utilizing projection data obtained from the selected radiation beams. In some configurations in which a weighting function takes values of 0 and 1 exclusively (or equivalently, 0 and some other constant value), the reconstruction is performed without the use of redundant projection data from unselected conjugate rays of the selected radiation beams. In some configurations, reconstructing an image of the object comprises utilizing the windowed and filtered projection data from which redundancy has been removed through the use of the vitual/general Tam-window.

In some configurations, radiation source 14 is an x-ray source. Also, in some configurations, step 104 can include utilizing a window function written:

$$w(\alpha, \beta, \gamma) = \begin{cases} 1 & \text{while } \alpha = \min(\alpha_0, \alpha_0', \alpha_0''), \\ 0 & \text{otherwise,} \end{cases} \text{ where:}$$

$\alpha_0$ is a cone angle of a radiation beam passing through pixel P; $\alpha_0'$ and $\alpha_0''$ are cone angles of two other x-ray beams passing through pixel P oppositely in relation to the radiation beam having cone angle $\alpha_0$; $\beta$ is a view angle; and $\gamma$ is a fan angle.

In some configurations of the present invention, step 104 comprises utilizing a window function written:

$$w(\alpha, \beta, \gamma) = \begin{cases} 1 & \text{while } \alpha = \min(\alpha_0, \alpha_c), \\ 0 & \text{otherwise,} \end{cases} \quad (15)$$

where $\alpha_c = \alpha_0'$ or $\alpha_c = \alpha_0''$, a cone angle of a radiation beam passing through a pixel P oppositely in relation to a direct ray having cone angle $\alpha_0$; $\alpha$ is a cone angle; $\beta$ is a view angle; and $\gamma$ is a fan angle. In some of these configurations, the method further includes a row-wise fan-to-parallel rebinning of the projection data. Also, in some of these configurations, the direct ray having cone angle $\alpha_0$ has fan angle $\gamma_0$ and view angle $\beta_0$; $\beta_c = \beta_0 - \pi + 2 \cdot \gamma_0$ and $\gamma_c = -\gamma_0$ while $0 < \beta_0 \leq \pi$; $\beta_c = \beta_0 + \pi + 2 \cdot \gamma_0$ and $\gamma_c = -\gamma_0$ while $-\pi < \beta_0 \leq 0$; and cone angles $\alpha_c$ are obtained through geometrical calculations.

In some configurations of the present invention, step 104 comprises utilizing a window function written:

$$\tilde{w}(\alpha, \beta, \gamma; k) = \frac{|\tan \alpha_c|^k}{|\tan \alpha_0|^k + |\tan \alpha_c|^k}, \quad (16)$$

where: $\alpha_0$ is a cone angle of a radiation beam passing through pixel P; $\alpha_c$ is a cone angle of a radiation beam passing through a pixel P oppositely in relation to a direct ray having cone angle $\alpha_0$; $\alpha$ is a cone angle; $\beta$ is a view angle; $\gamma$ is a fan angle; and k is an integer. In some configurations in which redundancy configuration is emphasized, k is at least 64. However, if k is smaller than 64, the virtual/general Tam-window disclosed herein performs very well for redundancy normalization. Moreover, k can be decreased significantly with variable helical pitch and detector row number.

In some configurations, windowing and image reconstruction are performed, for example, by one or more of image reconstructor 34, and/or computer 36, utilizing storage device 38. The resulting images can be displayed on display 42.

Configurations of virtual/general Tam-windows disclosed herein are different from that of the Tam-window, but provide the same result, i.e., the discarding of all redundant projection data in a helical CB reconstruction. Configurations of virtual/general Tam-windows disclosed herein can thus be utilized in all CB reconstructions in which a Tam-window is currently used, such as the exact helical CB shift-invariant filtered backprojection reconstruction algorithm proposed by Katsevich in "Analysis of an exact inversion algorithm for spiral cone-beam CT," Physics in Medicine & Biology, vol. 47, pp. 2583–2598, 2002, approximate helical shift-invariant FBP reconstruction algorithms, and the PI method and its derivatives.

It will thus be appreciated that configurations of the present invention provide alternatives to the well-known Tam-window for CB volumetric CT utilizing exact and approximate helical CB reconstruction methods to handle data redundancy. Moreover, by avoiding a discrete sampling of the Tam-window, artifacts introduced in tomographic images are substantially reduced.

While the invention has been described in terms of various specific embodiments, those skilled in the art will recognize that the invention can be practiced with modification within the spirit and scope of the claims.

What is claimed is:

1. A method for reconstructing an image of an object utilizing a cone-beam volumetric computed tomographic imaging apparatus, said method comprising:
   helically scanning the object with a radiation source utilizing the cone-beam volumetric computed tomographic imaging apparatus;
   selecting radiation beams emitted by the radiation source passing through a pixel P having a smallest cone angle in comparison with that of the conjugate rays of the radiation beam; and
   reconstructing an image of the object utilizing projection data obtained from the selected radiation beams.

2. A method in accordance with claim 1 wherein said reconstructing an image of the object is performed without the use of redundant projection data from unselected conjugate rays of the selected radiation beams.

3. A method in accordance with claim 1 wherein the radiation source is an x-ray radiation source.

4. A method in accordance with claim 1 wherein said selecting radiation beams passing through a pixel P having a smallest cone angle in comparison with that of the conjugate rays of the radiation beam comprises utilizing a window function written:

$$w(\alpha, \beta, \gamma) = \begin{cases} 1 & \text{while } \alpha = \min(\alpha_0, \alpha'_0, \alpha''_0), \\ 0 & \text{otherwise,} \end{cases} \text{ where:}$$

$\alpha_0$ is a cone angle of a radiation beam passing through pixel P;
$\alpha_0'$ and $\alpha_0''$ are cone angles of two other x-ray beams passing through pixel P oppositely in relation to the radiation beam having cone angle $\alpha_0$; and
$\beta$ is a view angle; and
$\gamma$ is a fan angle.

5. A method in accordance with claim 1 wherein said selecting radiation beams passing through a pixel P having a smallest cone angle in comparison with that of the conjugate rays of the radiation beam comprises utilizing a weighting function $\tilde{w}(\ )$ written:

$$\tilde{w}(\alpha, \beta, \gamma) = \frac{f_k(\alpha_c)}{f_k(\alpha_0) + f_k(\alpha_c)}, \text{ where:}$$

$\alpha$ is a cone angle;
$\beta$ is a view angle;
$\gamma$ is a fan angle;
$\alpha_0$ is a cone angle of a radiation beam passing through pixel P;
$\alpha_0'$ and $\alpha_0''$ are cone angles of two other x-ray beams passing through pixel P oppositely in relation to the radiation beam having cone angle $\alpha_0$;
$\alpha_c = \alpha_0'$ or $\alpha_c = \alpha_0''$;
$f_k(\alpha)$ denotes a positive valued, monotonically increasing function of both $\alpha$ and k, wherein $f_k(\alpha)$ also has the property that $f_k(\alpha) \to \infty$ when $k \to \infty$; and
k is a positive integer.

6. A method in accordance with claim 1 wherein said selecting radiation beams passing through a pixel P having a smallest cone angle in comparison with that of the conjugate rays of the radiation beam comprises utilizing a window function written:

$$w(\alpha, \beta, \gamma) = \begin{cases} 1 & \text{while } \alpha = \min(\alpha_0, \alpha_c), \\ 0 & \text{otherwise,} \end{cases}$$

where:
$\alpha_c = \alpha_0'$ or $\alpha_c = \alpha_0''$, where $\alpha_c$ is a cone angle of a radiation beam passing through a pixel P oppositely in relation to a direct ray having cone angle $\alpha_0$;
$\alpha$ is a cone angle;
$\beta$ is a view angle; and
$\gamma$ is a fan angle.

7. A method in accordance with claim 6 wherein:
the direct ray having cone angle $\alpha_0$ has fan angle $\gamma_0$ and view angle $\beta_0$;
$\beta_c$, $\alpha_c$ and $\gamma_c$ represent the view angle, cone angle, and fan angle, respectively, of a conjugate ray;
$\beta_c = \beta_0 - \pi + 2 \cdot \gamma_0$ and $\gamma_c = -\gamma_0$ while $0 < \beta_0 \leq \pi$;
$\beta_c = \beta_0 + \pi + 2 \cdot \gamma_0$ and $\gamma_c = -\gamma_0$ while $-\pi < \beta_0 \leq 0$; and
cone angles $\alpha_c$ are obtained through geometrical calculations.

8. A method in accordance with claim 6 wherein $\gamma_0 = \gamma_c = 0$ and further comprising row-wise fan-to-parallel rebinning of the projection data, wherein a direct ray having cone angle $\alpha_0$ has fan angle $\gamma_0$, and $\gamma_c$ represents the fan angle of a conjugate ray.

9. A method in accordance with claim 8 wherein the object is a medical patient.

10. A method in accordance with claim 1 wherein said selecting radiation beams passing through a pixel P having a smallest cone angle in comparison with that of the con jugate rays of the radiation beam comprises utilizing a window function written:

$$\tilde{w}(\alpha, \beta, \gamma; k) = \frac{|\tan \alpha_c|^k}{|\tan \alpha_0|^k + |\tan \alpha_c|^k},$$

where:
- $\alpha_0$ is a cone angle of a radiation beam passing through pixel P;
- $\alpha_c$ is a cone angle of a radiation beam passing through a pixel P oppositely in relation to a direct ray having cone angle $\alpha_0$;
- $\alpha$ is a cone angle;
- $\beta$ is a view angle;
- $\gamma$ is a fan angle; and
- k is an integer.

11. A method in accordance with claim 10 wherein k is at least 64.

12. A method in accordance with claim 1 wherein the object is a medical patient.

13. A method in accordance with claim 12 wherein the radiation source is an x-ray radiation source.

14. A cone-beam volumetric computed tomographic imaging apparatus configured to:
- helically scan an object to be imaged with a radiation source;
- select radiation beams emitted by the radiation source passing through a pixel P having a smallest cone angle in comparison with that of conjugate rays of the radiation beam; and
- reconstruct an image of the object utilizing projection data obtained from the selected radiation beams.

15. An apparatus in accordance with claim 14 configured to reconstruct said image of the object without the use of redundant projection data from unselected conjugate rays of the selected radiation beams.

16. An apparatus in accordance with claim 14 wherein the radiation source is an x-ray radiation source.

17. An apparatus in accordance with claim 14 wherein to select radiation beams passing through a pixel P having a smallest cone angle in comparison with that of the conjugate rays of the radiation beam, said apparatus is configured to utilize a window function written:

$$w(\alpha, \beta, \gamma) = \begin{cases} 1 & \text{while } \alpha = \min(\alpha_0, \alpha_0', \alpha_0''), \\ 0 & \text{otherwise,} \end{cases}$$ where:

- $\alpha_0$ is a cone angle of a radiation beam passing through pixel P;
- $\alpha_0'$ and $\alpha_0''$ are cone angles of two other x-ray beams passing through pixel P oppositely in relation to the radiation beam having cone angle $\alpha_0$; and
- $\beta$ is a view angle; and
- $\gamma$ is a fan angle.

18. An apparatus in accordance with claim 14 wherein said to select radiation beams passing through a pixel P having a smallest cone angle in comparison with that of the conjugate rays of the radiation beam, said apparatus is configured to utilize a weighting function $\tilde{w}(\ )$ written:

$$\tilde{w}(\alpha, \beta, \gamma) = \frac{f_k(\alpha_c)}{f_k(\alpha_0) + f_k(\alpha_c)}, \text{ where:}$$

- $\alpha$ is a cone angle;
- $\beta$ is a view angle;
- $\gamma$ is a fan angle;
- $\alpha_0$ is a cone angle of a radiation beam passing through pixel P;
- $\alpha_0'$ and $\alpha_0''$ are cone angles of two other x-ray beams passing through pixel P oppositely in relation to the radiation beam having cone angle $\alpha_0$;
- $\alpha_c = \alpha_0'$ or $\alpha_c = \alpha_0''$;
- $f_k(\alpha)$ denotes a positive valued, monotonically increasing function of both $\alpha$ and k, wherein $f_k(\alpha)$ also has the property that $f_k(\alpha) \to \infty$ when $k \to \infty$; and
- k is a positive integer.

19. An apparatus in accordance with claim 14 wherein to select radiation beams passing through a pixel P having a smallest cone angle in comparison with that of the conjugate rays of the radiation beam, said apparatus is configured to utilize a window function written:

$$w(\alpha, \beta, \gamma) = \begin{cases} 1 & \text{while } \alpha = \min(\alpha_0, \alpha_c), \\ 0 & \text{otherwise,} \end{cases}$$

where:
- $\alpha_c = \alpha_0'$ or $\alpha_c = \alpha_0''$, where $\alpha_c$ is a cone angle of a radiation beam passing through a pixel P oppositely in relation to a direct ray having cone angle $\alpha_0$;
- $\alpha$ is a cone angle;
- $\beta$ is a view angle; and
- $\gamma$ is a fan angle.

20. An apparatus in accordance with claim 19 wherein:
- the direct ray having cone angle $\alpha_0$ has fan angle $\gamma_0$ and view angle $\beta_0$;
- $\beta_c$, $\alpha_c$ and $\gamma_c$ represent the view angle, cone angle, and fan angle, respectively, of a conjugate ray;
- $\beta_c = \beta_0 - \pi + 2 \cdot \gamma_0$ and $\gamma_c = -\gamma_0$ while $0 < \beta_0 \leq \pi$;
- $\beta_c = \beta_0 + \pi + 2 \cdot \gamma_0$ and $\gamma_c = -\gamma_0$ while $-\pi < \beta_0 \leq 0$; and
- cone angles $\alpha_c$ are obtained through geometrical calculations.

21. An apparatus in accordance with claim 20 wherein $\gamma_0 = \gamma_c = 0$ and said apparatus is further configured to perform row-wise fan-to-parallel rebinning of the projection data, wherein a direct ray having cone angle $\alpha_0$ has fan angle $\gamma_0$, and $\gamma_c$ represents the fan angle of a conjugate ray.

22. An apparatus in accordance with claim 14 wherein to select radiation beams passing through a pixel P having a smallest cone angle in comparison with that of the conjugate rays of the radiation beam, said apparatus is configured to utilize a window function written:

$$\tilde{w}(\alpha, \beta, \gamma; k) = \frac{|\tan \alpha_c|^k}{|\tan \alpha_0|^k + |\tan \alpha_c|^k},$$

where:
- $\alpha_0$ is a cone angle of a radiation beam passing through pixel P;

$\alpha_c$ is a cone angle of a radiation beam passing through a pixel P oppositely in relation to a direct ray having cone angle $\alpha_0$;
$\alpha$ is a cone angle;
$\beta$ is a view angle;
$\gamma$ is a fan angle; and
k is an integer.

23. A method in accordance with claim 22 wherein k is at least 64.

24. A method in accordance with claim 23 wherein the radiation source is an x-ray radiation source.

* * * * *